United States Patent [19]

Koenig et al.

[11] 4,131,751
[45] Dec. 26, 1978

[54] DIURETHANES

[75] Inventors: Karl-Heinz Koenig, Frankenthal; Ulrich Schirmer, Heidelberg; Bruno Wuerzer; Kurt Fett, both of Limburgerhof, all of Fed. Rep. of Germany

[73] Assignee: BASF Aktiengesellschaft, Ludwigshafen, Fed. Rep. of Germany

[21] Appl. No.: 818,523

[22] Filed: Jul. 25, 1977

[30] Foreign Application Priority Data

Jul. 28, 1976 [DE] Fed. Rep. of Germany ....... 2638897
Jun. 3, 1977 [DE] Fed. Rep. of Germany ....... 2725074

[51] Int. Cl.$^2$ ...................... C07C 125/04; A01N 9/20
[52] U.S. Cl. ......................................... 560/29; 71/111
[58] Field of Search ............................................... 560/29

[56] References Cited

U.S. PATENT DOCUMENTS

| | | | |
|---|---|---|---|
| 3,865,867 | 2/1975 | Olin et al. | 560/29 |
| 3,898,075 | 8/1975 | Freund et al. | 560/29 |
| 3,901,936 | 8/1975 | Boroschewski | 560/29 |
| 3,904,396 | 9/1975 | Boroschewski et al. | 560/29 |
| 3,904,669 | 9/1975 | Boroschewski et al. | 560/29 |
| 3,920,829 | 11/1975 | Rohr et al. | 560/29 |

*Primary Examiner*—James O. Thomas, Jr.
*Assistant Examiner*—G. T. Breitenstein
*Attorney, Agent, or Firm*—Keil, Thompson & Shurtleff

[57] ABSTRACT

New and valuable diurethanes of the formula

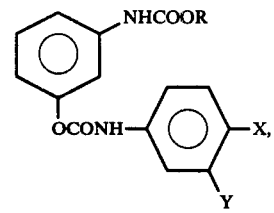

where R denotes lower alkyl, X/Y denote the combination fluorine/fluorine, fluorine/chlorine or chlorine/fluorine, and processes for controlling the growth of unwanted plants with these compounds.

7 Claims, No Drawings

DIURETHANES

The present invention relates to new and valuable diurethanes having an excellent herbicidal action, herbicides containing these compounds, and processes for controlling the growth of unwanted plants with these compounds.

It is known to use 3-isopropyl-2,1,3-benzothiadiazin(4)-one-2,2-dioxide for the selective control of unwanted broadleaved weeds (German 1,542,836).

A further compound of importance in agriculture is ethyl-N-(3-N'-phenylcarbamoyloxy)-phenyl carbamate (German Laid-Open Application DOS 1,567,151). The only crop in which this active ingredient is used is beet (Beta).

Diurethanes having a herbicidal action and containing a phenyl radical substituted by a fluorine atom or 2 chlorine atoms, e.g., ethyl-N-(3-N'-(4'-fluorophenylcarbamoyloxy)-phenyl carbamate (German Laid-Open Application DOS 1,567,151, German Published Application DAS 1,568,138), are known.

We have now found that 3-(N'-halofluorophenylcarbamoyloxyphenyl)-carbamates of the formula

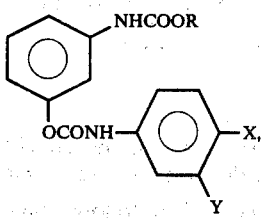

where R denotes lower alkyl (methyl, ethyl), and X/Y denote the combination fluorine/fluorine, fluorine/chlorine or chlorine/fluorine, have an excellent action on numerous important unwanted plants, and are tolerated well by crop plants, e.g., soybeans (*Glycine max.*). The new active ingredients are also tolerated excellently by other crop plants, e.g., ground nuts, beet and certain vegetable varieties, and acceptably by rice; consequently, these compounds may be employed in numerous crops, either individually or in combination with other herbicidal substances.

The new compounds may for instance be prepared by the following methods:

a) Reaction of N-(3-hydroxyphenyl)-urethanes (prepared in turn by conventional methods from m-aminophenol (German Laid-Open Application DOS 1,643,763) or 3-hydroxyphenyl isocyanate (British 1,153,261)) with halofluorophenyl isocyanates in the presence of a catalyst conventionally used for isocyanate reactions, e.g., tertiary amines (triethylamine, 1,4-diazabicyclo-(2,2,2)-octane), nitrogen-containing heterocycles (pyridine, 1,2-dimethylimidazole) and organic tin compounds (dibutyltin diacetate, dimethyltin dichloride), in the presence or absence of a solvent inert under the reaction conditions, e.g., hydrocarbons (ligroin, benzene, toluene, pentane, cyclohexane), halohydrocarbons (methylene chloride, dichloroethane, chlorobenzene), nitrohydrocarbons (nitrobenzene, nitromethane), nitriles (acetonitrile, butyronitrile, benzonitrile), ethers (diethyl ether, tetrahydrofuran, dioxane), esters (ethyl acetate, methyl propionate), ketones (acetone, methyl ethyl ketone) and amides (dimethylformamide, formamide) (German Laid-Open Application DOS 1,568,138) at temperatures of from 0° to 150° C., preferably from 40° to 100° C.

b) Reaction of N-(3-hydroxyphenyl)-urethanes or their alkali metal salts with halofluorophenylcarbamic acid chlorides (prepared by addition of hydrogen chloride to the appropriate isocyanates in accordance with Houben-Weyl, Methoden der organischen Chemie, VIII, 130, Georg Thieme-Verlag, Stuttgart, 4th ed., 1952), in the presence or absence of an acid binder, e.g., alkali metal hydroxides, alkali metal carbonates, alkali metal bicarbonates, alkaline earth metal oxides, alkaline earth metal hydroxides, alkaline earth metal carbonates, alkaline earth metal bicarbonates, and tertiary organic bases (e.g., triethylamine, pyridine, N,N-dimethylamine) in a solvent, e.g., water, alcohols (methanol, ethanol, isopropanol) or as listed under a) (German Laid-Open Applications DOS 1,568,138 and 1,568,621).

c) Reaction of m-nitrophenol with halofluorophenyl isocyanates (equivalent to method a)) or with halofluorophenylcarbamic acid chlorides (equivalent to method b)), subsequent reduction of the nitro group by known methods, e.g., hydrogenation, catalyzed by a noble metal such as platinum, palladium or Raney nickel, in a solvent as given under b), with the exception of nitrohydrocarbons and certain halohydrocarbons, followed by reaction with chlorocarbonic acid esters in the presence of an inorganic or organic base in a solvent (as under b)) (German Laid-Open Application DOS 1,568,621).

d) Reaction of N-(3-hydroxyphenyl)-urethanes with phosgene, advantageously in a solvent inert under the reaction conditions (as under a)) — if desired, with the addition of acid binders (as under b)) — to give the corresponding chlorocarbonic acid ester, which is then reacted with a halofluoroaniline analogously to method b) to give the desired end product (German Laid-Open Application DOS 1,593,523). Method a) is preferred.

The manufacture of the new diurethanes is illustrated by the following examples.

EXAMPLE 1

Ethyl-N-(3-(N'-3,4-difluorophenylcarbamoyloxy)-phenyl)-carbamate (No. 1)

18.1 g (0.1 mole) of ethyl-N-(3-hydroxyphenyl)-carbamate and 0.5 g of triethylamine in 150 ml of dry toluene are heated at 70°-80° C. 15.5 g (0.1 mole) of 3,4-difluorophenyl isocyanate is slowly dripped in and the mixture stirred for 3 hours at 100° C. After having been allowed to cool, the mixture is suction filtered and the residue recrystallized from ethyl acetate/petroleum ether. Yield: 22.0 g (66%); m.p.: 127°-130° C.

EXAMPLE 2

Methyl-N-(3-(N'-3-chloro-4-fluorophenylcarbamoyloxy)-phenyl)-carbamate (No. 9)

8.6 parts by weight of 3-chloro-4-fluorophenyl isocyanate is added to a solution of 8.4 parts of N-(3'-hydroxyphenyl)-methylcarbamate in 100 parts of tetrahydrofuran and one drop of dibutyltin diacetate.

After the mixture has stood for 20 hours it is concentrated, 80 parts of toluene is added to the residue, and the resultant mixture suction filtered. After drying, there is obtained 16.2 parts by weight of white crystals having a melting point of from 175°-177° C.

The following new diurethanes may be prepared analogously:

2. ethyl-N-(3-(N'-3-chloro-4-fluorophenylcarbamoyloxy)-phenyl)-carbamate, m.p. 133°–134° C.
3. ethyl-N-(3-(N'-3-fluoro-4-chlorophenylcarbamoyloxy)-phenyl)-carbamate, m.p. 155°–158° C.
8. methyl-N-(3-(N'-3,4-difluorophenylcarbamoyloxy)-phenyl)-carbamate, m.p. 161°–163° C.
9. methyl-N-(3-(N'-3-chloro-4-fluorophenylcarbamoyloxy)-phenyl)-carbamate, m.p. 175°–177° C.
10. methyl-N-(3-(N'-3-fluoro-4-chlorophenylcarbamoyloxy)-phenyl)-carbamate, m.p. 170°–173° C.

Preparation of the starting compounds

Recipe A 3-chloro-4-fluorophenyl isocyanate

At −10° to 0° C. and while stirring, a solution of 156 parts by weight of 3-chloro-4-fluoroaniline (J. Chem. Soc., 1928, 423) is metered into a solution of 250 parts by weight of phosgene in 1,000 parts by weight of toluene. The mixture is slowly heated to 110° C. (internal temperature), at which temperature it becomes clear.

The solvent is then distilled off at subatmospheric pressure. The crude isocyanate which remains is purified by vacuum distillation; b.p. (33 mm Hg): 108°–112° C.

The compound has the following structural formula:

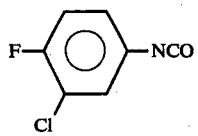

Analogously, phosgenation of 3-fluoro-4-chloroaniline (J. Chem. Soc., 1928, 423) gives a solid crude isocyanate which is purified by crystallization; m.p.: 39°–42° C.

The compound has the following structural formula:

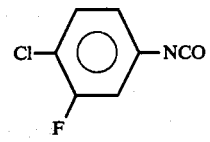

Recipe B 3,4-difluorophenyl isocyanate

At −10° to 0° and while stirring, 120 g of 3,4-difluoroaniline (J. Chem. Soc., 73, 5884–5, 1951) is metered into a solution of 180 parts by weight of phosgene in 1,100 parts by weight of chloronaphthalene. The reaction mixture is then slowly heated to 150° C. while passing in additional phosgene, and phosgenated for 2 hours at this temperature. Excess phosgene is expelled with nitrogen and the isocyanate distilled from the solution; b.p. (30 mm Hg): 79°–85° C.

The compound has the following structural formula:

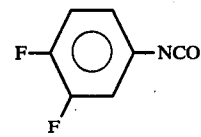

Experiments demonstrating the herbicidal action of the new diurethanes (biscarbamates)

The experiments which follow demonstrate the special nature of the active ingredients of the invention compared with chemically similar prior art compounds. The compounds used for comparison purposes were herbicidal diurethanes (compounds nos. 4, 5 and 7) and the closest commercial standard product from this class of compounds (no. 6). Compounds 11, 12, 13 and 14 have the following formulae:

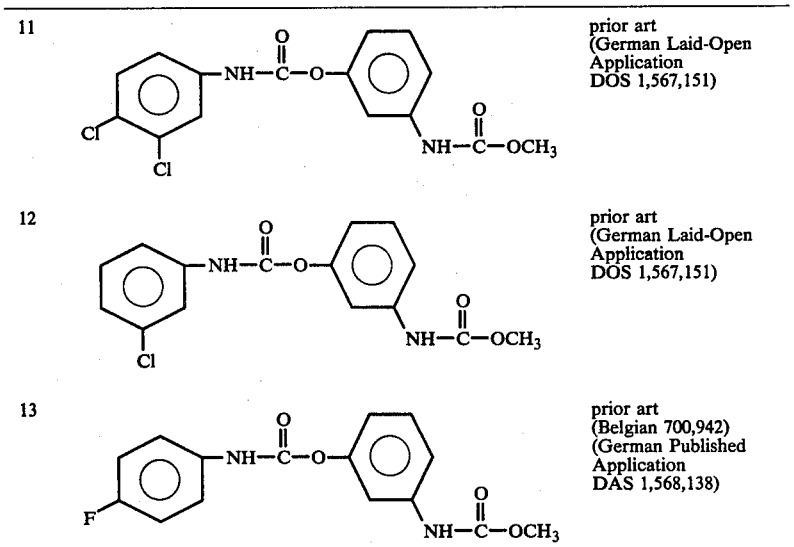

| | | |
|---|---|---|
| 14 | 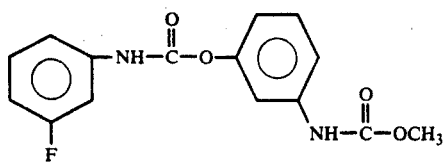 | prior art (German Laid-Open Application DOS 1,567,151) |

The series of experiments were carried out in the greenhouse and in the open.

I. Greenhouse experiments

Paraffined paper cups having a volume of 200 cm³ were filled with a sandy loam containing 1.5% humus, in which the test plants, separated by species, were sown (Table 1). As all the treatments were postemergence (leaf) treatments, the plants were grown to the desired size and growth stages. As a rule, the plants were treated when they had developed from 1 to 5 genuine leaves (in a few cases more). The agents were applied in water as distribution medium, with the aid of fine atomizing nozzles. Depending on the temperature requirements of the test plants, the experiments were carried out either in the cooler (15°–26° C.) or warmer (25°–40° C.) part of the greenhouse. The experimental period was from 2 to 4 weeks, during which the plants were regularly tended and their reaction to the various treatments was assessed. The tables below contain the substances investigated and the application rates in kg/ha of active ingredient. The scale for assessment was 0 to 100, 0 denoting no damage and 100 complete destruction.

II. Experiments in the open

The substances were applied to plots. The spray employed was a motor-driven plot spray mounted on a hitch. The active ingredients were emulsified in water as the distribution medium. Spraying took place after emergence of the plants and at various growth stages. The crop plants (Tables 7 and 8) were sown in rows. For the most part, weed growth was natural, but weed seeds were additionally scattered to increase the stand. The soil in the individual experiments was a sandy loam having a pH of 5 to 6 and containing 1 to 2% humus. All the experiments were run for several weeks. The action of the active ingredients on the crop and unwanted plants was recorded on the 0 to 100 scale.

Results

The comparative agent ethyl-N-(3-(N'-3,4-dichlorophenylcarbamoyloxy)-phenyl)-carbamate (compound no. 7) fell generally behind because of its middling to poor herbicidal action. The new compound no. 1 and active ingredient no. 2 according to the invention were clearly superior (Tables 3 and 7).

The same inferiority also applies to the monofluoro-substituted compound no. 4 employed for comparison purposes (Tables 2 and 7).

Comparative compound no. 5 was more active than the two abovementioned comparative agents, and embraced the weed spectrum controlled by the compounds of the invention, but the action per unit of active ingredient was less than that of new compound no. 1. This weakness was particularly evident in weeds such as *Stellaria media*, Sinapis species, Raphanus species and Veronica species which are important in Central European beet crops. Of importance for warmer regions is the superiority of the new compound in unwanted species such as Desmodium, Euphorbia and Solanum, to which reference was made above.

In view of the poor action of the comparative agents which are, due to their substitution, closest to the compounds of the invention, their more or less pronounced tolerance by crop plants is meaningless (Tables 4, 5 and 6).

The comparison with the unsubstituted compound no. 6 was therefore the only one of interest. Its herbicidal action was equivalent to that of the new compounds. Certain weaknesses in some species were on average cancelled out by its superiority in *Datura stramonium* (Tables 2 and 7).

However, the greenhouse experiments with various varieties of soybeans showed that the new compound no. 1 caused much less damage to the leaves than comparative agent no. 6 (Tables 4 and 5). Even known soybean herbicides cause damage to some species. As an example, 3-isopropyl-2,1,3-benzothiadiazinone-(4)-2,2-dioxide was investigated (Table 5). In these greenhouse experiments, compound no. 1 (according to the invention) was acceptable, whereas comparative agent no. 6 was not, on account of its much greater phytotoxicity.

With regard to tolerance by crop plants, sugar beet and rice tolerated compound no. 2 better than comparative agent no. 6 (Table 6).

The phytotoxicity of comparative agent no. 6 was pointed out in the introduction, and was clearly evident here. By contrast, the beets treated with new compound no. 1 showed hardly any effects of the herbicide (Tables 6, 7 and 8), a sign of its superior selectivity in this crop.

With reference to Tables 9 and 10, all the compounds investigated had a herbicidal action. However, if these results are scrutinized more closely, it will be seen that the new compounds are superior to the prior art compounds in a number of individual comparisons, either because of their superior herbicidal action or because they are better tolerated by crop plants. That this is so is unexpected and surprising, and is a special feature of the compounds according to the invention.

Table 1

| | List of plant names | |
|---|---|---|
| Botanical name | Abbreviation in tables | Common name |
| Amaranthus retroflexus | Amar. retr. | pigweed |
| Anthemis spp. | Anth. | chamomile |
| Arachis hypogaea | Arach. hyp. | peanuts |
| Beta vulgaris spp. alt. | Beta vulg. | sugarbeets |
| Brassica napus | — | rape |
| Chenopodium album | Chenop. album | lambsquarters |
| Chrysanthemum segetum | Saatwucherblume | corn marigold |

Table 1-continued

| Botanical name | List of plant names Abbreviation in tables | Common name |
|---|---|---|
| Datura stramonium | Datura str. | Jimsonweed |
| Desmodium tortuosum | Desm. tort. | Florida beggarweed |
| Euphorbia geniculata | Euph. gen. | South American member of the spurge family |
| Galinsoga spp. | Galin. spp. | — |
| Glycine max | — | soybeans |
| Gosspyium hirsutum | Gossp. hirs. | cotton |
| Helianthus annuus | | sunflowers |
| Ipomoea spp. | | morningglory (annual) |
| Lamium amplexicaule | | henbit |
| Matricaria chamomilla | Matric. cham. | wild chamomile |
| Matricaria spp. | Matr. | chamomile |
| Medicago sativa | Medic. sat. | alfalfa |
| Mercurialis annua | Mercur. annua | annual mercury |
| Oryza sativa | Oryza sat. | rice |
| Phaseolus vulgaris | Phaseol. vulg. | snapbeans |
| Polygonum aviculare | | prostrate knotweed |
| Polygonum convolvulus | Polyg. conv. | wild buckwheat |
| Raphanus raphanistrum | Raph. | wild radish |
| Sesbania exaltata | Sesb. exalt. | hemp sesbania (coffeeweed) |
| Setaria viridis | Set. virid. | green foxtail |
| Sinapis alba | | white mustard |
| Sinapis arvensis | Sinap. | wild mustard |
| Solanum nigrum | Solan. nigrum | black nightshade |
| Sorghum bicolor | Sorgh. bic. | wild cane |
| Spergula arvensis | Sper. arv. | corn spurry |
| Stellaria media | Stell. med. | chickweed |
| Veronica spp. | Veron. spp. | speedwell |
| Xanthium pennsylvanicum | Xanth. penns. | common cocklebur |
| Thlaspi arvense | | field pennycress |
| Triticum aestivum | | wheat |

Table 2

Herbicidal action of ethyl-N-(3-N'-(3', 4'-difluorophenyl)-carbamoyloxy)-phenyl)-carbamate; postemergence treatment in the greenhouse

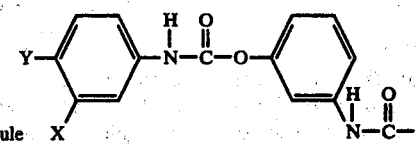

Basic molecule

| Substituents | | | Appl. | Unwanted plants and % destruction | | | | | | | | | |
|---|---|---|---|---|---|---|---|---|---|---|---|---|---|
| X | Y | Compound no. | rate kg/ha | Amar. retr. | Datura str. | Desm. tort. | Euph. gen. | Matric. cham. | Mercur. annua | Sesb. exalt. | Solan. nigrum | Veron. spp. | Set. virid. |
| F | F | 1 | 0.5 | 97 | — | 87 | 48 | 95 | 50 | 50 | 90 | 70 | 65 |
|  |  |  | 1.0 | 97 | 50 | 97 | 70 | 95 | 60 | 63 | 95 | 90 | 75 |
| F | H | 4 | 0.5 | 17 | — | 20 | 35 | 70 | 25 | 32 | 0 | 0 | 40 |
|  |  | prior art | 1.0 | 30 | 50 | 20 | 45 | 75 | 82 | 50 | 35 | 10 | 40 |
| H | F | 5 | 0.5 | 83 | — | 67 | 10 | 70 | 82 | 25 | — | 25 | 50 |
|  |  | prior art | 1.0 | 95 | 100 | 97 | 40 | 90 | 82 | 40 | 75 | 78 | 60 |
| H | H | 6 | 0.5 | 97 | — | 78 | 65 | 95 | 72 | 58 | 90 | 90 | 68 |
|  |  | prior art | 1.0 | 97 | 100 | 97 | 65 | 100 | 72 | 60 | 95 | 90 | 90 |

0 = no action
100 = complete destruction

Table 3

Further comparison of a chemically similar diurethane with ethyl-N-(3-N'-(3', 4'-difluorophenyl)-carbamoyloxy)-phenyl)-carbamate; postemergence treatment in the greenhouse

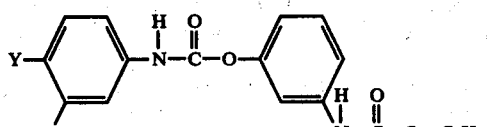

Basic molecule

| Substituents | | | Appl. | Unwanted plants and % destruction | | | | | |
|---|---|---|---|---|---|---|---|---|---|
| X | Y | Compound no. | rate kg/ha | Amar. retro. | Desmod. tort. | Euphorb. genic. | Sesb. exalt. | Setaria virid. | Xanth. penns. |
| F | F | 1 | 0.5 | 95 | 85 | 70 | 60 | 65 | — |
|  |  |  | 1.0 | 95 | 95 | 100 | 78 | 75 | 80 |
| Cl | Cl | 7 | 0.5 | 48 | 30 | 0 | 50 | 32 | — |
|  |  | prior art | 1.0 | 68 | 35 | 0 | 65 | 58 | 90 |

0 = no action
100 = complete destruction

Table 4

Tolerance of various soybean varieties to herbicidal diurethanes; leaf treatment in the greenhouse

| Compound no. | Appl. rate kg/ha | SRF 450 | Tracy | Lee 68 | Forrest | Bragg | Dare | Average for all varieties |
|---|---|---|---|---|---|---|---|---|
| 1 | 0.5 | 0 | 0 | 0 | 0 | 0 | 0 | 0 |
|   | 1.0 | 0 | 0 | 0 | 0 | 0 | 0 | 0 |
|   | 4.0 | 0 | 10 | 10 | 40 | 20 | 25 | 18 |
| 4 | 0.5 | 0 | 0 | 0 | 0 | 0 | 0 | 0 |
|   | 1.0 | 0 | 0 | 0 | 0 | 0 | 0 | 0 |
|   | 4.0 | 0 | 0 | 0 | 0 | 10 | 20 | 5 |
| 5 | 0.5 | 0 | 0 | 0 | 0 | 0 | 0 | 0 |
|   | 1.0 | 0 | 0 | 0 | 0 | 0 | 0 | 0 |
|   | 4.0 | 0 | 10 | 10 | 10 | 20 | 25 | 12 |
| 6 | 0.5 | 10 | 10 | 0 | 10 | 10 | 20 | 10 |
|   | 1.0 | 10 | 10 | 0 | 20 | 10 | 20 | 12 |
|   | 4.0 | 10 | 10 | 30 | 20 | 25 | 30 | 21 |

0 = no damage
100 = plants destroyed

Table 5

Tolerance of various soybean varieties in two growth stages to herbicidal diurethanes; leaf treatment in the greenhouse Soybean variety and % damage in stages I and II[+)]

| Compound no. | Appl. rate kg/ha | SRF 450 I | SRF 450 II | Dare I | Dare II | Bragg I | Bragg II | Forrest I | Forrest II | Lee 68 I | Lee 68 II | Tracy I | Tracy II | Hurrelbrink I | Hurrelbrink II |
|---|---|---|---|---|---|---|---|---|---|---|---|---|---|---|---|
| 1 | 1.0 | — | 8 | 5 | — | 10 | 0 | — | — | 0 | — | 10 | — | — | — |
|   | 2.0 | — | 8 | 5 | — | 10 | 0 | 5 | 5 | 0 | 0 | 10 | 0 | — | 2 |
|   | 4.0 | 5 | 8 | 5 | 10 | 10 | 0 | 5 | 5 | 8 | 10 | 10 | 0 | — | — |
| 7 | 1.0 | — | 5 | 5 | — | 15 | 0 | — | — | 0 | — | 10 | — | — | — |
|   | 2.0 | — | 5 | 10 | — | 15 | 0 | 15 | 2 | 0 | 0 | 10 | 0 | — | 0 |
|   | 4.0 | 8 | 5 | 10 | 5 | 15 | 0 | 15 | 2 | 0 | 2 | 10 | 10 | — | — |
| 6 | 1.0 | — | 2 | 15 | — | 15 | 0 | — | — | 5 | — | 15 | — | — | — |
|   | 2.0 | — | 2 | 15 | — | 15 | 5 | 70 | 25 | 10 | 20 | 15 | 0 | — | 10 |
|   | 4.0 | 30 | 2 | 40 | 10 | 30 | 5 | 70 | 25 | 20 | 25 | 20 | 0 | — | — |
| 3-isopropyl-2,1,3-benzo-thiadiazinone-(4)-2,2-dioxide (prior art) | 1.0 | — | 0 | 10 | — | 15 | 5 | — | — | 0 | — | 5 | — | — | — |
|   | 2.0 | — | 0 | 10 | — | 15 | 5 | 5 | 0 | 0 | 0 | 5 | 0 | — | 85 |
|   | 4.0 | 2 | 0 | 10 | 20 | 15 | 5 | 5 | 0 | 0 | 0 | 5 | 0 | — | — |

0 = no damage
[+)] I = undivided to first trifoliolate leaf
100 = plants destroyed
II = 1 1/2 to 2 trifoliolate leaves

Table 6

Tolerance of various herbicidal diurethanes by various crops; leaf treatment in the greenhouse Crop plants and % damage

| Compound no. | Appl. rate kg/ha | Arach. hyp. | Beta vulg. | Gossyp. hirs. | Oryza sat. | Phaseol. vulg. | Sorgh. bic. |
|---|---|---|---|---|---|---|---|
| 1 | 0.5 | 0 | 0 | 7 | 12 | — | — |
|   | 2.0 | 0 | 2 | 10 | 16 | 0 | 0 |
|   | 4.0 | 0 | 12 | 20 | 22 | 0 | 0 |
| 5 | 0.5 | 0 | 6 | 0 | 7 | — | — |
|   | 2.0 | 0 | 10 | 3 | 10 | 0 | 0 |
|   | 4.0 | — | 30 | 10 | 13 | 0 | 0 |
| 7 | 0.5 | 0 | 15 | — | 18 | — | — |
|   | 2.0 | 0 | 25 | 62 | 20 | — | 0 |
|   | 4.0 | — | 33 | 58 | 20 | — | 0 |
| 2 | 0.5 | 0 | 0 | — | 0 | — | — |
|   | 2.0 | 0 | 0 | 40 | 8 | — | 0 |
|   | 4.0 | — | 2 | 40 | 15 | — | 0 |
| 6 | 0.5 | 0 | 2 | 23 | 12 | — | — |
|   | 2.0 | 0 | 18 | 30 | 16 | 0 | 0 |
|   | 4.0 | 0 | 19 | 50 | 27 | 0 | 20 |

0 = no damage
100 = plants destroyed

Table 7

Herbicidal action and crop plant tolerance of diurethanes; postemergence treatment in the open Test plants and % damage

| Compound no. | Appl. rate kg/ha | Beta vulg. | Amar. retr. | Anth./ Matr. | Brassica napus+) | Cheuop. album | Galins. spp. | Medic. sat.+) | Polyg. conv. | Sinap./ raph. | Sper. arv. | Stell. med. |
|---|---|---|---|---|---|---|---|---|---|---|---|---|
| 1 | 0.5 | 0 | 98 | 67 | 88 | 87 | 99 | 85 | 68 | 87 | 75 | 82 |
|   | 1.0 | 1 | 99 | 77 | 99 | 93 | 100 | 78 | 81 | 97 | 92 | 98 |
| 4 | 0.5 | 0 | 5 | 2 | 46 | 42 | 85 | 45 | 0 | 20 | 20 | 75 |
|   | 1.0 | 0 | 6 | 11 | 63 | 57 | 92 | 45 | 3 | 35 | 52 | 85 |
| 5 | 0.5 | 0 | 95 | 55 | 89 | 83 | 95 | 60 | 55 | 58 | 80 | 60 |

Table 7-continued

Herbicidal action and crop plant tolerance of diurethanes; postemergence treatment in the open

| Compound no. | Appl. rate kg/ha | Beta vulg. | Amar. retr. | Anth./ Matr. | Brassica napus+) | Cheuop. album | Galins. spp. | Medic. sat.+) | Polyg. conv. | Sinap./ raph. | Sper. arv. | Stell med. |
|---|---|---|---|---|---|---|---|---|---|---|---|---|
|   | 1.0 | 1 | 100 | 81 | 97 | 94 | 98 | 73 | 90 | 88 | 97 | 86 |
| 6 | 0.5 | 1 | 91 | 54 | 76 | 82 | 80 | 55 | 97 | 67 | 83 | 40 |
|   | 1.0 | 8 | 98 | 73 | 95 | 95 | 83 | 74 | 98 | 84 | 99 | 88 |
| 7 | 0.5 | 5 | 66 | 37 | 14 | 18 | — | — | — | — | — | — |
|   | 1.0 | — | 78 | 61 | 46 | 32 | — | — | — | — | — | — |
| 2 | 0.5 | 4 | 87 | 71 | 74 | 62 | — | — | — | — | — | — |
|   | 1.0 | — | 93 | 87 | 99 | 76 | — | — | — | — | — | — |

0 = no damage
100 = plants destroyed
+) unwanted plant in beet

Table 8

Tolerance of various herbicidal diurethanes by sugarbeets; postemergence treatment in the open

| Compound no. | Appl. rate kg/ha | Test plant and % damage Beta vulgaris spp. alt. |
|---|---|---|
| 1 | 2.0 | 4 |
|   | 4.0 | 13 |
| 5 | 2.0 | 10 |
|   | 4.0 | 26 |
| 6 | 2.0 | 24 |
|   | 4.0 | 44 |

0 = no damage
100 = complete destruction

Table 9

Postemergence treatment in the greenhouse

| Test plants | Compound and % damage | | | | | |
|---|---|---|---|---|---|---|
|   | 8 | | 9 | | 11 prior art | |
| kg/ha | 1.0 | 2.0 | 1.0 | 2.0 | 1.0 | 2.0 |
| Arachis hypogaea | 0 | 5 | 0 | 0 | 0 | 5 |
| Beta vulgaris | 0 | 0 | 0 | 0 | 0 | 0 |
| Glycine max | 0 | 0 | 0 | 0 | 0 | 10 |
| Gossypium hirsutum | 3 | 15 | — | — | 35 | 40 |
| Euphorbia geniculata | — | — | 90 | 90 | 20 | 60 |
| Datura stramonium | 90 | 90 | — | — | 70 | 90 |
| Ipomoea spp. | 60 | 70 | 58 | 75 | 45 | 45 |
| Mercurialis annua | 100 | 100 | 75 | 95 | 0 | 0 |
| Sesbania exaltata | 57 | 70 | 70 | 90 | 45 | 45 |
| Setaria viridis | 78 | 95 | — | — | 40 | 40 |
| Sinapis alba | 60 | 82 | 80 | 87 | 45 | 45 |
| Solanum nigrum | 82 | 95 | — | — | 60 | 60 |
| Thlaspi arvense | — | — | 95 | 95 | 40 | 40 |

| | 8 | | 13 prior art | |
|---|---|---|---|---|
| | 1.0 | 2.0 | 1.0 | 2.0 |
| Arachis hypogaea | 0 | 5 | 0 | 5 |
| Glycine max | 0 | 0 | 0 | 0 |
| Helianthus annuus | 0 | 0 | 60 | 60 |
| Triticum aestivum | 7 | 7 | 30 | 30 |
| Chrysanthemum segetum | 95 | — | 0 | — |
| Datura stramonium | 90 | 90 | 70 | 90 |
| Mercurialis annua | 100 | 100 | 0 | 50 |
| Solanum nigrum | 82 | 95 | 22 | 36 |

| | 9 | | 13 prior art | |
|---|---|---|---|---|
| | 1.0 | 2.0 | 1.0 | 2.0 |
| Arachis hypogaea | 0 | 0 | 0 | 5 |
| Beta vulgaris | 0 | 0 | 5 | 5 |
| Glycine max | 0 | 0 | 0 | 0 |
| Lamium amplexicaule | 80 | 100 | 70 | 95 |
| Mercurialis annua | 75 | 95 | 0 | 50 |
| Thlaspi arvense | 95 | 95 | 95 | 95 |

| | 8 | | 14 prior art | |
|---|---|---|---|---|
| | 1.0 | 2.0 | 1.0 | 2.0 |
| Arachis hypogaea | 0 | 5 | 0 | 0 |
| Beta vulgaris | 0 | 0 | 0 | 0 |
| Glycine max | 0 | 0 | 0 | 0 |
| Datura stramonium | 90 | 90 | 0 | 10 |
| Ipomoea spp. | 68 | 70 | 10 | 40 |
| Mercurialis annua | 100 | 100 | 0 | 0 |
| Sesbania exaltata | 57 | 75 | 10 | 20 |
| Setaria viridis | 78 | 95 | 20 | 35 |
| Solanum nigrum | 82 | 95 | 0 | 10 |

| | 9 | 12 prior art |
|---|---|---|
| | 1.0 | 1.0 |
| Arachis hypogaea | 0 | 0 |
| Beta vulgaris | 0 | 5 |
| Glycine max | 0 | 10 |
| Chrysanthemum segetum | 95 | 20 |
| Euphorbia geniculata | 90 | 50 |
| Lamium amplexicaule | 80 | 100 |
| Mercurialis annua | 75 | 30 |
| Sesbania exaltata | 70 | 80 |

0 = no damage
100 = complete destruction

Table 10

Postemergence treatment in the open

| Test plants | Compound and % damage | |
|---|---|---|
|   | 8 | 11 prior art |
| kg/ha | 1.0 | 1.0 |
| Beta vulgaris | 10 | 0 |
| Anthemis/Matricaria | 75 | 30 |
| Brassica napus (as unwanted plant) | 100 | 50 |
| Chenopodium album | 78 | 50 |
| Polygonum convolvulus | 70 (0.75 kg/ha) | 50 (0.75 kg/ha) |
| Raphanus raphanistrum/ Sinapis arvensis | 92 | 45 |

| | 9 | 11 prior art |
|---|---|---|
| | 1.0 | 1.0 |
| Anthemis/Matricaria | 67 | 30 |
| Brassica napus | 96 | 50 |
| Chenopodium album | 90 | 50 |
| Galinsoga parviflora | 100 | 100 |
| Lamium amplexicaule | 95 | 60 |

| | 9 | 12 prior art |
|---|---|---|
| | 1.0 | 1.0 |
| Amaranthus retroflexus | 90 | 65 |
| Chenopodium album | 90 | 90 |
| Galinsoga parviflora | 100 | 100 |
| Polygonum aviculare | 80 | 20 |
| Raphanus raphanistrum/ Sinapis arvensis | 100 | 100 |
| Thlaspi arvense | 90 | 90 |

| | 8 | 13 prior art |
|---|---|---|
| | 1.0 | 1.0 |
| Beta vulgaris | 10 | 12 |
| Glycine max | 2 | 0 |
| Brassica napus (as unwanted plant) | 100 | 89 |
| Raphanus raphanistrum/ Sinapis arvense | 92 | 79 |

| | 9 | | 13 prior art | |
|---|---|---|---|---|
| | 0.5 | 1.0 | 0.5 | 1.0 |
| Glycine max | 0 | 0 | 0 | 0 |
| Amaranthus retroflexus | 80 | 90 | 76 | 91 |
| Brassica napus (as unwanted plant) | 94 | 96 | 67 | 89 |
| Chenopodium album | 82 | 90 | 74 | 88 |
| Raphanus raphanistrum/ Sinapis arvensis | 95 | 100 | 52 | 79 |
| Thlspi arvense | 50 | 90 | 0 | 50 |

| | 8 | 14 prior art |
|---|---|---|
| | 1.0 | 1.0 |
| Anthemis/Matricaria | 75 | 30 |
| Raphanus raphanistrum | 92 | 70 |

0 = no damage
100 = complete destruction

The herbicides according to the invention may be sprayed directly onto the leaves of the crop plants. It is also possible to eliminate unwanted plants by postdirected or layby applications. In this case, the spray is directed in such a manner that the leaves of the crop plants are not — or only slightly — touched, and the smaller weeds are fully contacted. This method is particularly important for the treatment of low-growing unwanted plants in bush or tree crops.

In view of the application possibilities, the herbicides according to the invention or compositions containing them may not only be used in the crops listed in the tables but also in a much wider range of crops for removing unwanted plants. The amount of active ingredient applied may vary from 0.1 to 15 kg/ha and more, depending on the weeds to be controlled. The following crops may be mentioned by way of example:

| Botanical name | Common name |
|---|---|
| Allium cepa | onions |
| Ananas comosus | pineapple |
| Asparagus officinalis | asparagus |
| Avena sativa | oats |
| Beta vulgaris spp. rapa | fodder beets |
| Beta vulgaris esculenta | table beets, red beets |
| Brassica napus var. napus | rape |
| Brassica napus var. napobrassica | |
| Brassica napus var. rapa | turnips |
| Brassica napus var. silvestris | |
| Camellia sinensis | tea plants |
| Carthamus tinctorius | safflower |
| Citrus limon | lemon |
| Citrus maxima | grapefruit |
| Citrus reticulata | |
| Citrus sinensis | orange trees |
| Coffea arabica (Coffea canephora, Coffea liberica) | coffee plants |
| Cucumis melo | melons |
| Cucumis sativus | cucumber |
| Cynodon dactylon | Bermudagrass in turf and lawns |
| Daucus carota | carrots |
| Elaeis guineensis | oil palms |
| Fragaria vesca | strawberries |
| helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (n. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Pennisetum glaucum | |
| Petroselinum crispum spp. tuberosum | parsley |
| Picea abies | norway spruce |
| Abies alba | fir trees |
| Pinus spp. | pine trees |
| Pisum sativum | English peas |
| Prunus avium | cherry trees |
| Prunus domestica | plum trees |
| Prunus persica | peach trees |
| Pyrus communis | pear trees |
| Ribes sylvestre | redcurrants |
| Ribes uva-crispa | |
| Ricinus communis | |
| Saccharum officinarum | sugar cane |
| Secale cereale | rye |
| Sesamum indicum | sesame |
| Solanum tuberosum | Irish potatoes |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

The following list contains herbicides which, in admixture with the compounds of the invention, contribute toward an improvement in action over a wider range of plant species or intensify the action per unit of active ingredient:

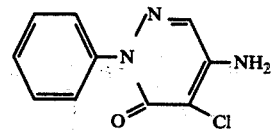

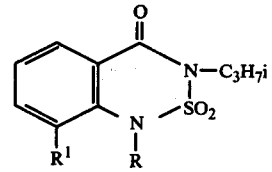

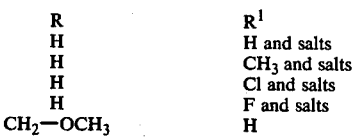

| R | R¹ |
|---|---|
| H | H and salts |
| H | CH₃ and salts |
| H | Cl and salts |
| H | F and salts |
| CH₂—OCH₃ | H |

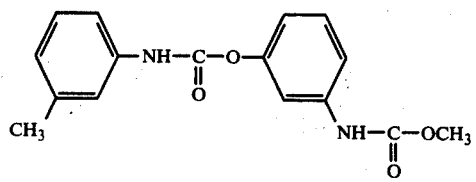

-continued
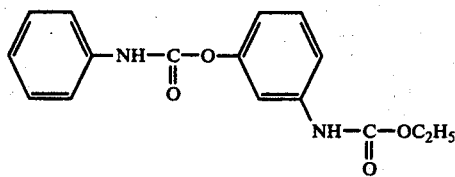
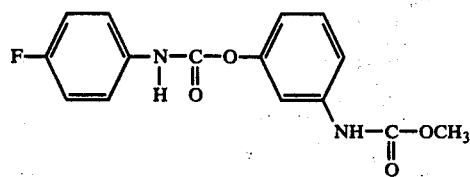
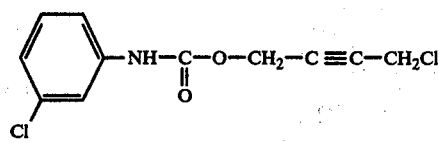
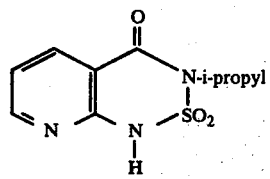
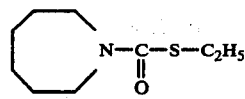
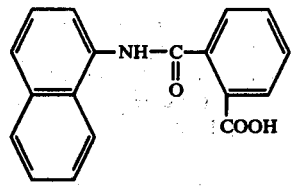
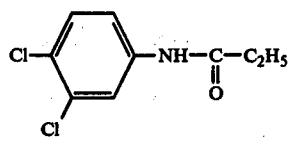
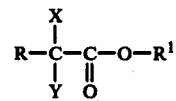
| R | X | Y | R¹ |
|---|---|---|---|
| CH₃ | Cl | Cl | Na |
|  | Cl | H | CH₃ |
| 4-Cl-C₆H₄-CH₂— |  |  |  |
|  | H | H | H and salts |
| C₆H₅-C(O)-N(H)-O— |  |  |  |
|  | H | CH₃ | CH₃ |
| 2,4-Cl₂-C₆H₃-O-C₆H₄-O— |  |  |  |

-continued
| | | | |
|---|---|---|---|
| 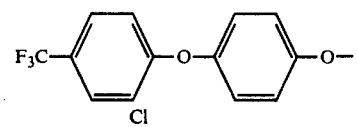 | H | CH$_3$ | Na |
| 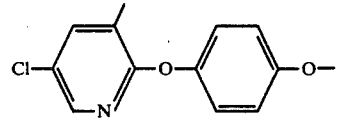 | H | CH$_3$ | Na |
| 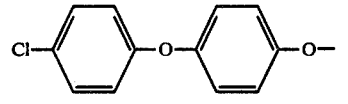 | H | CH$_3$ | CH$_2$-i-Propyl |
| 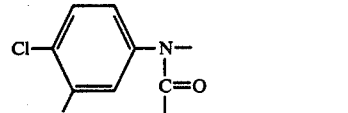 | H | CH$_3$ | C$_2$H$_5$ |
| 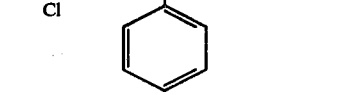 | H | CH$_3$ | i-Propyl |
| 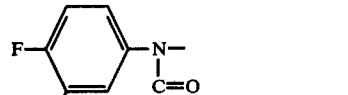 | H | CH$_3$ | CH$_3$ |
| 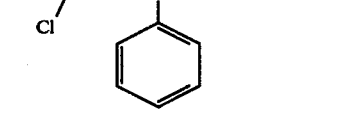 | Cl | Cl | Na |
| 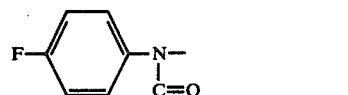 | | | |
| 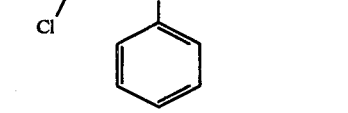 | | | |
| 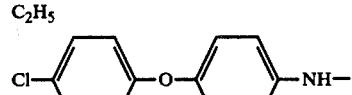 | | | |
| 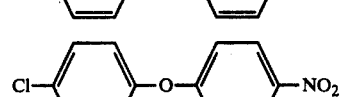 | H | CH$_3$ | Na |

-continued

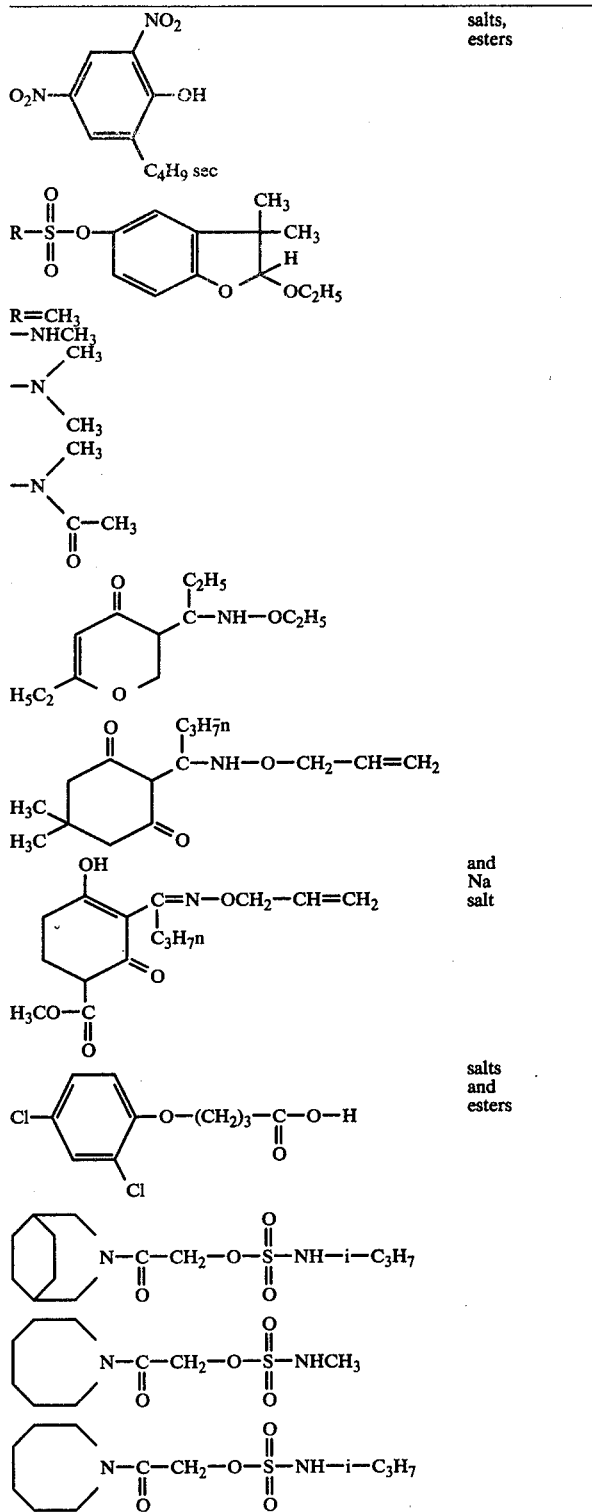

It is useful to be able to apply the compounds of the invention either alone or in combination with other herbicides, in admixture with other crop protection agents, for example agents for combatting pests or phytopathogenic fungi, and growth regulators. Of further interest is the fact that the compounds of the invention may be mixed with solutions of mineral fertilizers used to eliminate trace element or nutritional deficiencies.

Application may be effected for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenol polyglycol ethers, alkylaryl polyester alcohols, isotridecyl alcohols, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

There may be added to the compositions or individual active ingredients oils of various types, wetting agents or adherents, herbicides, fungicides, nematocides, insecticides, bactericides, trace elements, fertilizers, antifoams (e.g., silicones), growth regulators, antidotes and other herbicidally effective compounds.

These agents may be added to the herbicides according to the invention in a ratio by weight of from 1:10 to 10:1. The same applies to oils, wetting agents and adherents, fungicides, nematocides, insecticides, bactericides, antidotes and growth regulators.

EXAMPLE 3

90 parts by weight of compound 1 is mixed with 10 parts by weight of N-methyl-α-pyrrolidone. A mixture is obtained which is suitable for application in the form of very fine drops.

EXAMPLE 4

20 parts by weight of compound 2 is dissolved in a mixture consisting of 80 parts by weight of xylene, 10 parts by weight of the adduct of 8 to 10 moles of ethylene oxide to 1 mole of olefic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 5

20 parts by weight of compound 3 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 6

20 parts by weight of compound 2 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 7

20 parts by weight of compound 3 is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 8

.3 parts by weight of compound 1 is intimately mixed with 97 parts by weight of particulate kaolin. A dust is obtained containing 3% by weight of the active ingredient.

EXAMPLE 9

30 parts by weight of compound 2 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 10

40 parts by weight of compound 1 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt% of active ingredient.

EXAMPLE 11

20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:

1. Diurethanes of the formula

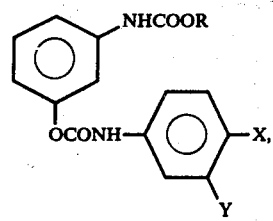

where R denotes lower alkyl, and X/Y denote the combination fluorine/fluorine, fluorine/chlorine or chlorine/fluorine.

2. Ethyl-N-(3-(N'-3,4-difluorophenylcarbamoyloxy)-phenyl)-carbamate.
3. Ethyl-N-(3-(N'-3-chloro-4-fluorophenylcarbamoyloxy)-phenyl)-caramate.
4. Ethyl-N-(3-(N'-3-fluoro-4-chlorophenylcarbamoyloxy)-phenyl)-carbamate.
5. Methyl-N-(3-(N'-3,4-difluorophenylcarbamoyloxy)-phenyl)-carbamate.
6. Methyl-N-(3-(N'-3-chloro-4-fluorophenylcarbamoyloxy)-phenyl)-carbamate.
7. Methyl-N-(3-(N'-fluoro-4-chlorophenylcarbamoyloxy)-phenyl)-carbamate.

* * * * *

UNITED STATES PATENT AND TRADEMARK OFFICE
CERTIFICATE OF CORRECTION

PATENT NO. : 4,131,751
DATED : December 26, 1978
INVENTOR(S) : Karl-Heinz Koenig et al It is certified that error appears in the above-identified patent and that said Letters Patent are hereby corrected as shown below:

IN THE HEADING:

[30] Foreign Application Priority Data

Jul. 28, 1976 should read --- August 28, 1976 ---.

Col. 24, line 18 (Claim 3)

"caramate" should read --- carbamate ---.

Signed and Sealed this

Eleventh Day of September 1979

[SEAL]

Attest:

LUTRELLE F. PARKER
Attesting Officer
Acting Commissioner of Patents and Trademarks